(12) United States Patent
Wiechers

(10) Patent No.: US 8,979,358 B2
(45) Date of Patent: Mar. 17, 2015

(54) MIXING DEVICE FOR LIQUID CHROMATOGRAPHY

(75) Inventor: Joachim Wiechers, Planegg (DE)

(73) Assignee: Dionex Softron GmbH, Germering (DE)

( * ) Notice: Subject to any disclaimer, the term of this patent is extended or adjusted under 35 U.S.C. 154(b) by 1058 days.

(21) Appl. No.: 13/058,177

(22) PCT Filed: Jul. 31, 2009

(86) PCT No.: PCT/DE2009/001076
§ 371 (c)(1),
(2), (4) Date: Mar. 23, 2011

(87) PCT Pub. No.: WO2010/015238
PCT Pub. Date: Feb. 11, 2010

(65) Prior Publication Data
US 2011/0188341 A1 Aug. 4, 2011

(30) Foreign Application Priority Data
Aug. 8, 2008 (DE) .......................... 10 2008 037 008

(51) Int. Cl.
*B01F 5/06* (2006.01)
*B01D 15/16* (2006.01)
*G01N 30/34* (2006.01)

(52) U.S. Cl.
CPC .............. *B01D 15/16* (2013.01); *B01F 5/0614* (2013.01); *G01N 30/34* (2013.01); *G01N 2030/347* (2013.01)
USPC ........... 366/339; 422/500; 422/501; 422/502; 436/180

(58) Field of Classification Search
CPC ......... B01F 5/0609; B01F 5/6014; B01F 5/00
USPC .................... 422/500–502; 366/339; 436/180
See application file for complete search history.

(56) References Cited

U.S. PATENT DOCUMENTS

| 4,202,635 A * | 5/1980 | Hendrickson .............. 366/162.3 |
| 6,379,625 B1 | 4/2002 | Zuk, Jr. |
| 2003/0192677 A1 | 10/2003 | Rong |

FOREIGN PATENT DOCUMENTS

| DE | 203 10 555 U1 | 9/2003 |
| JP | 4-204373 | 7/1992 |
| JP | 2003-270226 A | 9/2003 |
| JP | 2007-132873 A | 5/2007 |

OTHER PUBLICATIONS

PCT, Written Opinion of the International Search Authority for PCT Application No. PCT/DE2009/001076 dated Nov. 12, 2009 (5 pages).

* cited by examiner

*Primary Examiner* — Jyoti Nagpaul

(57) ABSTRACT

A mixing device for liquid chromatography for the radial mixing of at least two fluids comprises a tubular mixing line, and a helical flow-guiding element arranged in the mixing line. One or more spacing elements located within an interior region of the mixing line are adapted to maintain a predetermined distance between the outer sides of the helical flow-guiding element and an inner wall of the mixing line. A mixing unit according to the present invention may include such a radial mixing device, with a longitudinal mixing device being connected downstream from this radial mixing device.

17 Claims, 3 Drawing Sheets

MIXING DEVICE FOR LIQUID CHROMATOGRAPHY

TECHNICAL FIELD OF THE INVENTION

The invention relates to a mixing device for liquid chromatography for the radial mixing of at least two fluids, in particular, for the mixing of at least two eluents in high-performance liquid chromatography. In addition, the invention relates to a mixing unit for liquid chromatography comprising such a radial mixing device together with a longitudinal mixing device.

BACKGROUND OF THE INVENTION

In liquid chromatography, in particular high-performance liquid chromatography (HPLC), there is often the requirement for mixing, as homogeneously as possible, at least two different eluents according to a desired proportioning. This mixing ratio could also vary, in particular, over time. Typically, during the mixing of two eluents, two separate fluid flows that are each generated by a pump are fed to a T-piece by means of two tubular lines or capillaries. After the T-piece, there should be a homogeneous mixture of the two eluents corresponding to the specified mixture ratio.

During this mixing process, an error in the flow of one of the two pumps always leads to an error in the mixing ratio. For example, if reciprocating pumps are used, then typically after each stroke of each pump, a proportioning error occurs, so that a mixing wave appears along the axial course of the flow of the mixed eluent. In addition to this axial mixing wave, there is often also the problem that the two fluids are not uniformly mixed in the radial direction of the eluent flow, that is, a direction perpendicular to the direction of eluent flow. This applies at least for the part of the eluent mixture in the vicinity of the joining of the two eluent flows at the T-piece.

For generating an eluent flow that is mixed as uniformly as possible, it is known to use so-called active mixing chambers. A stirring element that is usually magnetically driven turns in an active mixing chamber, wherein an eluent composition is held constant within the mixing volume. The effect of a short-time pump error is thus reduced by a corresponding factor as a function of the mixer volume and is washed out with an exponential decrease at the outlet of the mixer.

In addition to active mixing chambers, so-called static, longitudinal mixers are known that are based on the principle of dividing the incoming overall flow into several parallel sub-flows, wherein the sub-flows cover flow paths of different lengths and are then joined together again. A mixing error that also exists in the individual sub-flows and is present over time and thus also in the axial flow direction therefore appears at the joining with correspondingly smaller amplitude and a corresponding time delay.

If the mixing ratio changes periodically, in particular for the use of reciprocating pistons, and if the volume of the longitudinal mixer is so large that the volume of a whole period can be held in the mixer, then mixer errors are averaged out in an especially effective way.

If the flow at the inlet of a longitudinal mixer is still unmixed (inhomogeneous) in the radial direction, then these radial inhomogeneities can negatively affect the effectiveness of the longitudinal mixer.

Therefore, it is known to connect a radial mixing device upstream from a longitudinal mixing device.

In practice, radial, passive mixing devices are used that are made from a tubular mixer line in which a flow-guiding or turbulence-forming element is inserted. Indeed, radial mixing would also be achieved by diffusion along a line for the fluid mixture, but this effect is so weak and the radial dimensions of the flow of the fluid mixture are so large that radial mixing just through diffusion would require too long a time span or too large an axial length of the flow of the fluid mixture. In contrast, the use of one or more flow-guiding or turbulence-forming elements in the line for the fluid mixture leads to a significantly quicker homogenization of the fluid mixture. The flow of the fluid mixture here could be generated in a turbulent or laminar way. As flow-guiding elements, in practice, in particular, so-called helix mixers are used. Such a mixing device is known, for example, from JP 2007 13 28 73 A. For this mixer that was developed for the mixing of one eluent with one test sample in liquid chromatography, a spiral-shaped or helical element is used in a tubular part. The helix has, however, only a few windings, wherein the diameter of this spiral-shaped or helical element corresponds essentially to the inner diameter of the affected line. The effect of this mixing device thus is that the flow of fluid to be mixed is set into a helical rotational motion, wherein the fluid is mixed, due to the helical rotational motion, after leaving the mixer element or flow-guiding or turbulence-forming element. However, the effectiveness of a mixer constructed in this way is, in part, insufficient.

In addition, static, radial mixing devices are known in which a helical, twisted tubular line is provided, with the fluid mixture to be mixed flowing through this line. The action of such a radial mixing device is that, in particular, the fast portion of the laminar flow within the helical tubular line, that is, the center (in the cross section of the flow), experiences a centrifugal force. This force drives this part of the flow out from the center in the direction of the tube inner wall onto the outer side of the helical tubular line. A flow must then flow back into the center from the more slowly flowing edge layers, in particular, the portions close to the tube inner wall onto the inner side of the helical profile of the tubular line, wherein a thorough radial mixture is then produced.

SUMMARY OF THE INVENTION

The present invention provides a radial mixing device that has an improved mixing effect and simultaneously a structurally simple construction. In addition, the invention provides a mixing unit which includes such a radial mixing device and a downstream longitudinal mixing device.

The invention operates according to the principle that the effectiveness of a radial mixing device with a helical flow-guiding element can be improved in that the flow-guiding element does not contact, with its outer periphery, the inner wall of the tubular mixing line, thus leaving an opening in the helical flow-guiding element in the vicinity of the inner wall of the tubular mixing line. For this purpose, spacing means may be provided that guarantee a predetermined spacing between the radially outer end side turned toward the inner wall of the mixing line in the helical wall of the flow-guiding element, and the inner wall of the tubular mixing line.

Providing such openings in the helical flow-guiding element causes the fluid mixture to be mixed in a radial direction, while passing through the region in the tubular mixing line in which the flow-guiding element is arranged. This mixing in a radial direction is in addition to the mixing occasioned by the helical rotation of the fluids along the helical flow guiding element.

The spacing means can be formed by advantageously periodic changes in the radius of the helical wall with respect to the longitudinal axis of the flow-guiding element (what is meant here is thus the spacing of a point on the longitudinal outer side of the helical wall of the flow-guiding element from its longitudinal axis), wherein the points or short sub-regions of the helical wall that feature the maximum radius interact with the inner wall of the mixing line for the positioning of the flow-guiding element in the inner space (interior volume) of the mixing line. A flow-guiding element that is created in this way and simultaneously realizes the spacing means can be produced easily and economically.

According to one embodiment of the invention, the changes in the radius of the helical wall of the flow-guiding element define spacing elements whose radii correspond essentially to the inner diameter of the mixing line, wherein the other regions of the wall of the helical flow-guiding element have a constant, smaller radius. In principle, however, the change in the radius of the helical wall of the flow-guiding element could have an arbitrary shape. All that is to be taken into consideration in this particular embodiment is that between the two sub-spaces that are defined by the wall in the inner space of the mixing line, sufficiently large overflow openings are created that guarantee sufficient radial mixing.

The predetermined spacing between the inner wall of the mixing line and the longitudinal outer sides of the flow-guiding element here lies advantageously in a range from 5-20% of the inner diameter of the tubular mixing line. In other words, the outer diameter of the helical flow-guiding element equals 60-90% of the inner diameter of the mixing line.

According to one preferred embodiment of the invention, the inner diameter of the tubular mixing line equals 0.2 mm to 1.0 mm, wherein a range from 0.4 mm to 0.6 mm has proven to be especially suitable.

Because the radial mixing is already realized in an effective way during the passage through the flow-guiding element, according to the invention, advantageously a minimum number of windings of the flow-guiding element is provided. The minimum number of windings dependent on the inner diameter of the mixing line equals six at a diameter of 0.2 mm, 10 at an inner diameter of 0.3 mm, 20 at an inner diameter of 0.5 mm, and 30 at an inner diameter of 1 mm. The required minimum number of windings for intermediate values for the inner diameter can be determined through linear interpolation between the previously mentioned points.

According to one embodiment of the invention, the flow-guiding element or wall could be produced from a planar, thin, strip-shaped element, advantageously a metallic sheet. The strip-shaped element could have, on its side edges, projections that form the spacing elements, wherein the spacing of the outer edges of the spacing elements at the opposite sides of the strip-shaped element perpendicular to the longitudinal axis of the strip-shaped element corresponds essentially to the inner diameter of the mixing line. Such a strip-shaped element could be twisted about its longitudinal axis for forming a helix. The material of the strip-shaped element must be selected so that sufficient plastic deformability is guaranteed for the twisting about the longitudinal axis.

For this purpose, the strip-shaped element advantageously has a thickness in the range from 0.02 mm to 0.06 mm, advantageously in the range from 0.03 mm to 0.05 mm.

Such a passive radial mixing device is also suitable, in particular, for realizing a mixing unit that simultaneously also guarantees a longitudinal mixing of the flow of fluid for liquid chromatography. For this purpose, the radial mixing device according to the invention is connected upstream to a longitudinal mixing device.

A mixing unit constructed in this way is also suitable for the mixing of a flow of fluid made of at least two fluids to be mixed, with this flow being generated by the alternating, axial feeding of the at least two fluids to be mixed. This allows, in particular, the use of a single pump, wherein either one or the other of the two fluids to be mixed is fed to a tubular line in a time alternating fashion.

The suitability of a mixing unit with a radial mixing unit connected upstream from a longitudinal mixing unit for a flow of fluid that is generated in this way and is made from at least two fluids to be mixed can be explained in that the axial, sharp separation of the two fluids is not maintained while flowing through a tubular line, but instead is expanded in the axial direction corresponding to the parabolic speed profile. This results in a radial structure made up of concentric rings. These radial inhomogeneities are eliminated to the greatest possible extent by the radial mixing device, so that the downstream longitudinal mixer can optimally develop its longitudinal mixing ability.

The volume of the longitudinal mixing device is here advantageously selected to be significantly larger than the volume of the radial mixing device, advantageously at least by a factor of 5, highly advantageously by at least a factor of 7.

These and other advantages and features of the invention will be apparent from the following description of illustrative embodiments, considered along with the accompanying drawings.

DESCRIPTION OF ILLUSTRATIVE EMBODIMENTS

Figure 1:
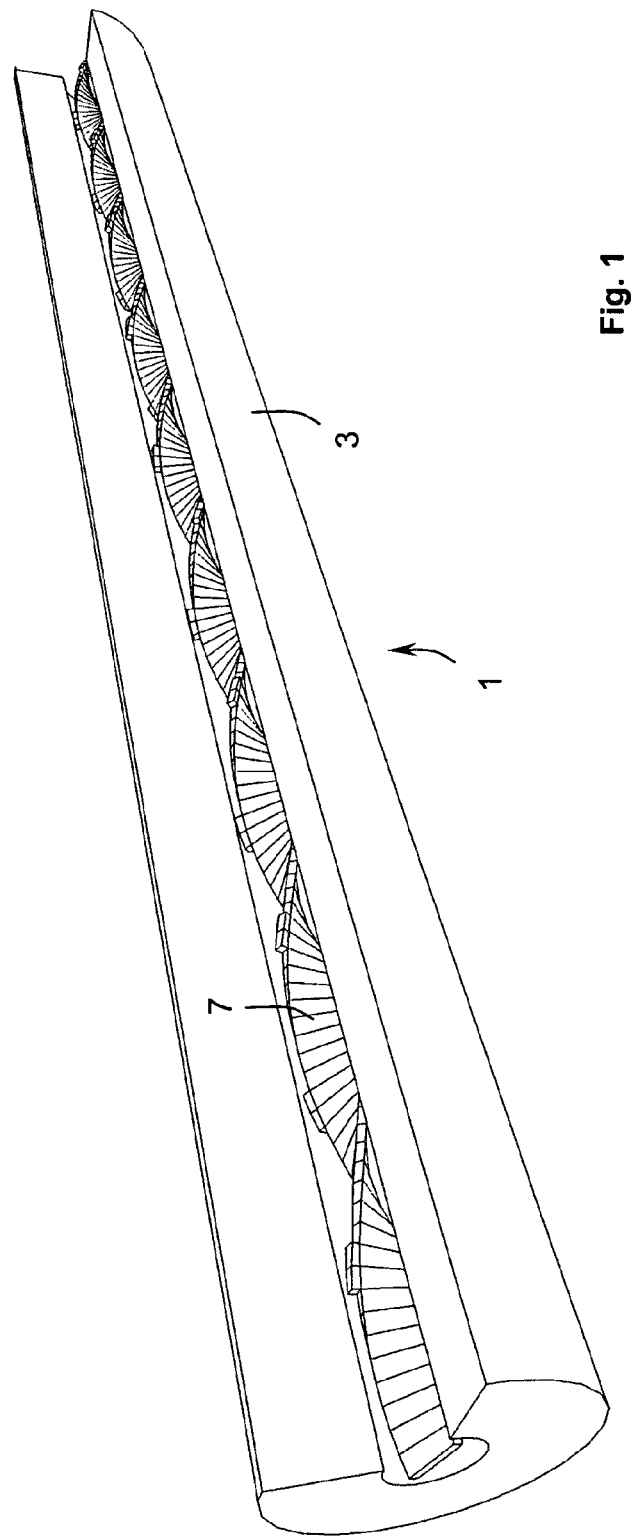
FIG. 1 is a perspective, partially cut-away, schematic diagram of a radial mixing device according to the invention.

The radial mixing device 1 shown in FIG. 1 comprises a tubular mixing line 3 that can have a straight construction, as shown in FIG. 1. Obviously, however, the mixing line 3 could also be curved.

Figure 3:
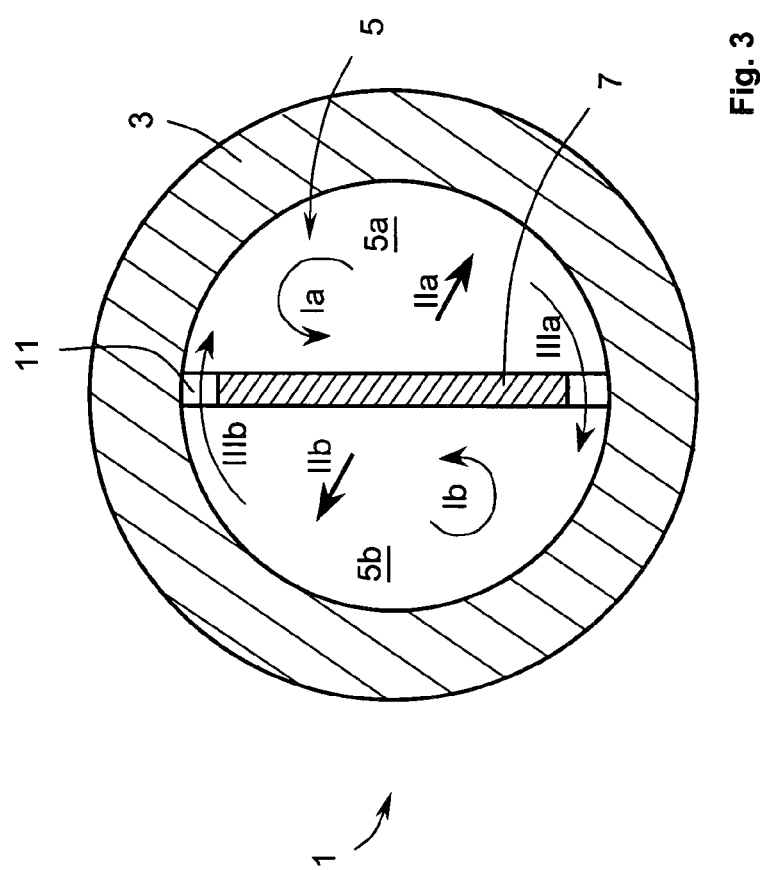
FIG. 3 is a schematic cross section through the radial mixing device in FIG. 1 with the course of flow indicated by various arrows.

As shown in FIG. 3, in the inner space (interior volume) 5 of the mixing line 3 there is a flow-guiding element or wall 7 that has a helical structure. In the shown embodiment, the helical flow-guiding element 7 has four complete 360° windings.

Figure 2:
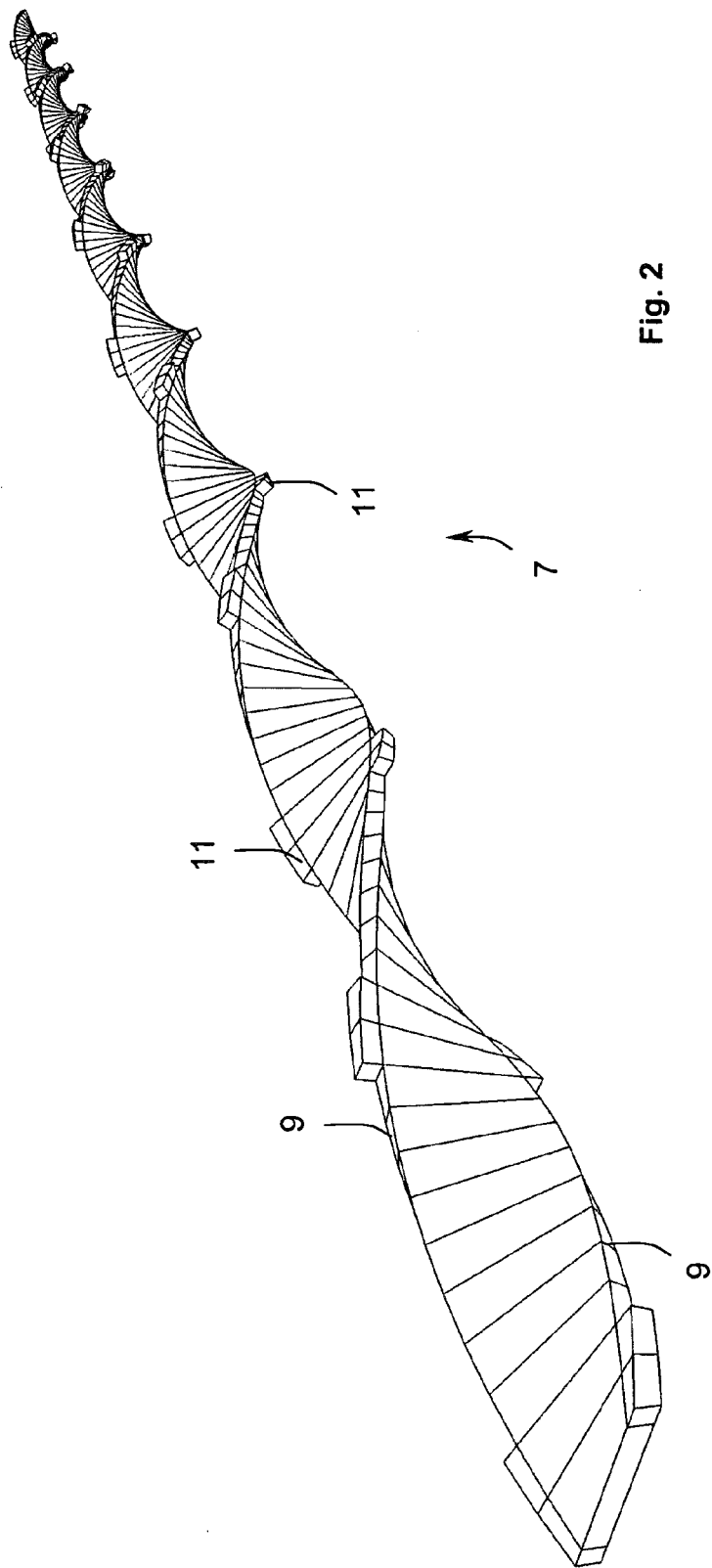
FIG. 2 is a perspective view of the flow-guiding element in FIG. 1.

The helical flow-guiding element 7 shown in perspective separately in FIG. 2 is produced from a planar, thin, strip-shaped element that was twisted about its longitudinal axis by a corresponding rotational angle equaling, in the shown embodiment, 4×360°=1440°. The planar strip has spacing elements 11 on its longitudinal outer sides 9. The spacing elements 11 can be provided, as shown in FIG. 2, at positions of the longitudinal outer sides 9 opposite each other. Obviously, however, the spacing elements 11 could also be provided offset on the appropriate longitudinal outer sides 9. The maximum diameter of the helical flow-guiding element 7 specified by the spacing elements 11 corresponds essentially to the inner diameter of the tubular mixing line 3, so that the completely produced flow-guiding element 7 can be introduced later into the inner space 5 of the mixing line 3, for example, by sliding or feeding into this space.

The inner diameter of the mixing line 3 advantageously lies in the range from 0.2 mm to 1 mm, wherein, in practice, usually a diameter from 0.3 mm to 0.6 mm will be selected. This applies at least for the field of HPLC.

The flow-guiding element 7 is advantageously produced from a material that allows sufficient plastic deformation during the production of the helical structure. A thin metal sheet is particularly suitable as the material. The thickness of such a metal sheet can lie in the range from 0.02 mm to 0.06 mm, wherein a range from 0.03 mm to 0.05 mm has proven advantageous.

The action of a radial mixing device created in this way will be explained schematically with reference to FIG. 3: due to the coiled structure of the flow-guiding element 7, a thorough radial mixing that is indicated by the arrows Ia, IIa and Ib and IIb, respectively, is produced for a fluid that is to be mixed and is fed to one end of the mixing device 1 and is made from at least two components in the two sub-spaces 5a and 5b, respectively, of the inner space 5. In each of the two halves 5a and 5b of the inner space 5, wherein these halves are partitioned by the wall representing the flow-guiding element 7, a helical-shaped track is formed in the axial direction for the appropriate sub-flow. The large length of the coil leads in most cases (but as a function of the geometry of the arrangement) to the formation of a laminar flow profile. This has the effect that, in particular, the fast parts of the laminar flow, that is, the portions of the flow in the centers of the two halves 5a, 5b of the inner space 5 of the mixing line, experience centrifugal forces (indicated by the arrows IIa, IIb), wherein these halves have crescent-shaped cross sections. These forces drive the flow out from the centers of the halves 5a, 5b with crescent-shaped cross sections in the direction toward the inner wall of the tubular mixing line 3. Fluid must then flow from the more slowly flowing edge layers of the flow in the halves 5a, 5b of the inner space 5 back in the direction toward the center of the halves 5a, 5b (arrows Ia, Ib).

In this way, because a gap remains between the inner wall of the mixing line 3 and the longitudinal outer sides 9 of the flow-guiding element 7 by means of the spacing element 11, an exchange of the fluid between both halves 5a, 5b of the inner space 5 with crescent-shaped cross sections (arrows IIIa, IIIb) is realized across the entire axial extent of the flow-guiding element 7 (apart from the areas sealed off by the spacing elements 11). This flow through openings in flow guiding element 7 (the openings in this case defined by the gap between the outer sides 9 of the flow-guiding element 7 and the inner wall of mixing line 3 in regions along the length of the flow-guiding element 7 between spacing elements 11) also produces an excellent mixing effect between the crescent-shaped volumes 5a and 5b.

In practice, the flow-guiding element 7 can consist of a metal, as already explained above. Through etching, the spacing elements 11 can be produced at the outer sides 9 of the initially planar strip. Instead of projection-like spacing elements 11, the planar strip could also be produced with an arbitrary, for example, wave-shaped width. After the twisting of the planar strip, only the maximum radius of the helical wall must correspond essentially to the inner diameter of the mixing line 3.

According to this principle, in practice, a radial mixing device is produced whose mixing line has an inner diameter of 0.5 mm. The flow-guiding element was realized with a length of 240 mm for 150 windings.

The spacing between the longitudinal outer sides 9 of the flow-guiding element 7 and the inner wall of the mixing line 3, that is, the height of the spacing element 11, equaled 15% of the inner diameter of the mixing line 3, i.e., the diameter of the helical flow-guiding element in areas between the spacing elements 11 equaled 70% of the inner diameter of the mixing line 3. With such a radial mixing device, excellent mixing results were achieved.

The spacing means, however, can be generated also or additionally by a corresponding geometry of the inner space of the mixing line. For example, a helical flow-guiding element with constant diameter could be used that is smaller in the desired way than the inner diameter of the mixing line. The mixing line with initially constant cross section can then be easily deformed at a few positions after the insertion of the flow-guiding element, so that, in the deformed areas, an essentially coaxial fixing of the flow-guiding element is realized.

In practice, in order to mix a flow of fluid made from at least two elements as completely as possible, it is desirable to perform both a radial mixing and also a longitudinal mixing. Such a complete mixing unit (not shown) can have a radial mixing device 1 according to FIGS. 1-3, with a longitudinal mixing unit of a known type being connected downstream from this radial mixing device.

It was determined that such a mixing unit is also suitable for the mixing of flows of fluids from at least two components, with this device being generated such that one of the at least two fluids is fed alternately. Initially, this leads to a flow of fluid that alternately leads exclusively one of the at least two components in the axial direction. At the axial joining position, however, due to the influence of the flow in one tube line, radial inhomogeneities are produced with respect to the mixing ratio. Due to the provision of a radial mixing device according to the invention, these radial inhomogeneities are equalized to the greatest possible extent. The subsequent longitudinal mixing device can effectively achieve a completely thorough mixing.

As used herein, whether in the above description or the following claims, the terms "comprising," "including," "carrying," "having," "containing," "involving," and the like are to be understood to be open-ended, that is, to mean including but not limited to. Any use of ordinal terms such as "first," "second," "third," etc., in the claims to modify a claim element does not by itself connote any priority, precedence, or order of one claim element over another, or the temporal order in which acts of a method are performed. Rather, unless specifically stated otherwise, such ordinal terms are used merely as labels to distinguish one claim element having a certain name from another element having a same name (but for use of the ordinal term).

The above described preferred embodiments are intended to illustrate the principles of the invention, but not to limit the scope of the invention. Various other embodiments and modifications to these preferred embodiments may be made by those skilled in the art without departing from the scope of the present invention.

The invention claimed is:

1. A mixing device for radially mixing at least two eluents in liquid chromatography, the mixing device comprising:
 (a) a tubular mixing line having an inner surface defining an interior volume;
 (b) a helical flow-guiding wall located in the interior volume of the mixing line, the helical flow-guiding wall being helical about a longitudinal axis of the tubular mixing line and extending longitudinally along at least a portion of the length of the tubular mixing line, the helical flow-guiding wall also having an elongated shape in transverse section perpendicular to the longitudinal axis of the tubular mixing line so as to define two sub-volumes within the interior volume of the tubular mixing line; and (c) a number of spacing elements located within the interior volume of the mixing line and spaced apart along at least a portion of the length of the helical flow-guiding wall, each spacing element comprising a maximum radius portion of the helical flow-guiding wall and extending to the inner surface of the mixing line so as to maintain a predetermined distance between an outer edge of the helical flow-guiding wall and the inner surface of the mixing line in an adjacent region along the length of the helical flow-guiding wall in which adjacent region the helical flow-guiding wall has a radius less than the maximum radius portion.

2. The mixing device of claim 1 wherein the predetermined distance is between 5 percent and 20 percent of an inner diameter of the mixing line.

3. The mixing device of claim 1 wherein the mixing line has an inner diameter of between 0.2 mm to 1.0 mm.

4. The mixing device of claim 1 wherein the mixing line has an inner diameter of between 0.4 mm to 0.6 mm.

5. The mixing device of claim 1 wherein the number of windings of the helical flow-guiding wall is dependent on the inner diameter of the mixing line and comprises six windings where the inner diameter of the mixing line is substantially equal to 0.2 mm, ten windings where the inner diameter of the mixing line is substantially equal to 0.3 mm, twenty windings where the inner diameter of the mixing line is substantially equal to 0.5 mm, and thirty windings where the inner diameter of the mixing line is substantially equal to 1.0 mm, and wherein the minimum number of windings for intermediate values for the inner diameter of the mixing line corresponds to the value determined by linear interpolation between the minimum number of winding values for inner diameters of 0.2 mm, 0.3 mm, 0.5 mm, and 1.0 mm.

6. The mixing device of claim 1 wherein:
(a) the helical flow-guiding wall is produced from a planar, strip-shaped, metallic sheet with opposite side edges having projections that form the spacing elements;
(b) the dimension of the metallic sheet in a direction perpendicular to the longitudinal axis thereof from a spacing element on one side of the sheet to a spacing element on the opposite side of the sheet is substantially equal to an inner diameter of the mixing line; and
(c) the strip-shaped metallic sheet is twisted about its longitudinal axis to form the helical shape.

7. The mixing device of claim 6 wherein the strip-shaped metallic sheet has a thickness between 0.02 mm and 0.06 mm.

8. The mixing device of claim 6 wherein the strip-shaped metallic sheet has a thickness between 0.03 mm and 0.05 mm.

9. A mixing unit for mixing at least two fluids in liquid chromatography, the mixing unit comprising:
(a) a radial mixing device comprising:
(i) a tubular mixing line having an inner surface defining an interior volume;
(ii) a helical flow-guiding wall located in the interior volume of the mixing line, the helical flow-guiding wall being helical about a longitudinal axis of the tubular mixing line and extending longitudinally along at least a portion of the length of the tubular mixing line, the helical flow-guiding wall also having an elongated shape in transverse section perpendicular to the longitudinal axis of the tubular mixing line so as to define two sub-volumes within the interior volume of the tubular mixing line; and
(iii) a number of spacing elements located within the interior volume of the mixing line and spaced apart along at least a portion of the length of the helical flow-guiding wall, each spacing element comprising a maximum radius portion of the helical flow-guiding wall and extending to the inner surface of the mixing line so as to maintain a predetermined distance between an outer edge of the helical flow-guiding wall and the inner surface of the mixing line in an adjacent region along the length of the helical flow-guiding wall in which adjacent region the helical flow-guiding wall has a radius less than the maximum radius portion; and
(b) a longitudinal mixing device connected to receive fluids which have passed through the radial mixing device.

10. The mixing unit of claim 9 wherein the volume of the longitudinal mixing device is greater than the volume of the radial mixing device.

11. The mixing unit of claim 10 wherein the volume of the longitudinal mixing device is at least five times as large as the volume of the radial mixing device.

12. The mixing unit of claim 10 wherein the volume of the longitudinal mixing device is at least seven times as large as the volume of the radial mixing device.

13. A mixing device for radially mixing at least two eluents in liquid chromatography, the mixing device comprising:
(a) a tubular mixing line having an inner surface defining an interior volume;
(b) a helical flow-guiding wall located in the interior volume of the mixing line, the helical flow-guiding wall being helical about a longitudinal axis of the tubular mixing line and extending longitudinally along at least a portion of the length of the tubular mixing line, the helical flow-guiding wall also having an elongated shape in transverse section perpendicular to the longitudinal axis of the tubular mixing line so as to define two sub-volumes within the interior volume of the tubular mixing line; and
(c) a number of flow mixing openings in the helical flow-guiding wall, each flow mixing opening being defined between an outer edge of the helical flow-guiding wall and an adjacent portion of the inner surface of the mixing line and having a predetermined height in the transverse dimension of the helical flow-guiding wall, the flow mixing openings being spaced apart along the length of the helical flow-guiding wall between spacing elements comprising portions of the flow-guiding wall which extend to the inner surface of the mixing line.

14. The mixing device of claim 13 wherein the predetermined height is between 5 percent and 20 percent of an inner diameter of the mixing line.

15. The mixing device of claim 13 wherein the mixing line has an inner diameter of between 0.2 mm to 1.0 mm.

16. The mixing device of claim 13 wherein the mixing line has an inner diameter of between 0.4 mm to 0.6 mm.

17. The mixing device of claim 13 wherein:
(a) the helical flow-guiding wall is produced from a planar, strip-shaped metallic sheet;
(b) the flow mixing openings are formed at the outer edge of the strip-shaped metallic sheet; and
(c) the strip-shaped metallic sheet is twisted about its longitudinal axis to form the helical shape.

* * * * *